United States Patent
Carus et al.

(10) Patent No.: US 7,822,598 B2
(45) Date of Patent: Oct. 26, 2010

(54) SYSTEM AND METHOD FOR NORMALIZATION OF A STRING OF WORDS

(75) Inventors: Alwin B. Carus, Waban, MA (US); Thomas J. DePlonty, III, Melrose, MA (US)

(73) Assignee: Dictaphone Corporation, Stratford, CT (US)

( * ) Notice: Subject to any disclaimer, the term of this patent is extended or adjusted under 35 U.S.C. 154(b) by 690 days.

(21) Appl. No.: 11/068,493

(22) Filed: Feb. 28, 2005

(65) Prior Publication Data

US 2005/0192792 A1      Sep. 1, 2005

Related U.S. Application Data

(60) Provisional application No. 60/547,797, filed on Feb. 27, 2004.

(51) Int. Cl.
   *G06F 17/27*   (2006.01)
(52) U.S. Cl. .............................. 704/9; 704/1
(58) Field of Classification Search .................... 704/9, 704/10, 1; 707/4–6
   See application file for complete search history.

(56) References Cited

U.S. PATENT DOCUMENTS

| | | | |
|---|---|---|---|
| 4,477,698 A | | 10/1984 | Szlam et al. |
| 4,965,763 A | | 10/1990 | Zamora |
| 5,253,164 A | | 10/1993 | Holloway et al. |
| 5,325,293 A | | 6/1994 | Dorne |
| 5,327,341 A | | 7/1994 | Whalen et al. |
| 5,392,209 A | | 2/1995 | Eason et al. |
| 5,526,443 A | * | 6/1996 | Nakayama ................... 382/229 |
| 5,544,360 A | | 8/1996 | Lewak et al. .................... 707/1 |
| 5,576,954 A | * | 11/1996 | Driscoll ........................ 707/3 |
| 5,640,553 A | * | 6/1997 | Schultz .......................... 707/5 |
| 5,664,109 A | * | 9/1997 | Johnson et al. ................. 705/2 |
| 5,799,268 A | * | 8/1998 | Boguraev ....................... 704/9 |
| 5,809,476 A | | 9/1998 | Ryan |
| 5,832,450 A | | 11/1998 | Myers et al. .................... 705/3 |
| 5,842,196 A | * | 11/1998 | Agarwal et al. ................. 707/2 |
| 5,937,422 A | * | 8/1999 | Nelson et al. ................ 715/531 |
| 5,970,463 A | | 10/1999 | Cave et al. |
| 6,014,663 A | * | 1/2000 | Rivette et al. .................. 707/4 |

(Continued)

OTHER PUBLICATIONS

F. Song et al., A Graphical Interface to a Semantic Medical Information System, *Journal of Foundations of Computing and Decision Sciences*, 22(2), 1997.

(Continued)

*Primary Examiner*—Douglas C Godbold
(74) *Attorney, Agent, or Firm*—Wolf, Greenfield & Sacks, P.C.

(57) ABSTRACT

The present invention relates generally to a system and method for categorization of strings of words. More specifically, the present invention relates to a system and method for normalizing a string of words for use in a system for categorization of words in a predetermined categorization scheme. A method for adaptive categorization of words in a predetermined categorization scheme may include receiving a string of text, tagging the string of text, and normalizing the string of text. Normalization may be performed with a three-stage algorithm including a literal match processing stage, an approximation match processing stage, and a nearest neighbor match processing stage. The normalized string of text can be compared to a number of sequences of text in the predetermined categorization scheme.

2 Claims, 7 Drawing Sheets

U.S. PATENT DOCUMENTS

| | | | |
|---|---|---|---|
| 6,021,202 A | 2/2000 | Anderson et al. | |
| 6,052,693 A * | 4/2000 | Smith et al. | 707/104.1 |
| 6,055,494 A * | 4/2000 | Friedman | 704/9 |
| 6,088,437 A | 7/2000 | Amick | |
| 6,182,029 B1 * | 1/2001 | Friedman | 704/9 |
| 6,192,112 B1 | 2/2001 | Rapaport et al. | |
| 6,292,771 B1 | 9/2001 | Haug et al. | |
| 6,321,224 B1 * | 11/2001 | Beall et al. | 707/5 |
| 6,347,329 B1 | 2/2002 | Evans | |
| 6,405,165 B1 | 6/2002 | Blum et al. | |
| 6,430,557 B1 * | 8/2002 | Gaussier et al. | 707/5 |
| 6,434,547 B1 | 8/2002 | Mishelevich et al. | |
| 6,438,533 B1 | 8/2002 | Spackman et al. | |
| 6,553,385 B2 | 4/2003 | Johnson et al. | 707/104.1 |
| 6,915,254 B1 | 7/2005 | Heinze et al. | 704/9 |
| 6,947,936 B1 | 9/2005 | Suermondt et al. | 707/7 |
| 7,016,895 B2 * | 3/2006 | Dehlinger et al. | 707/5 |
| 7,124,144 B2 | 10/2006 | Christianson et al. | 707/102 |
| 7,139,695 B2 * | 11/2006 | Castellanos | 704/4 |
| 7,185,001 B1 * | 2/2007 | Burdick et al. | 707/3 |
| 2002/0007285 A1 | 1/2002 | Rappaport | 705/2 |
| 2002/0022956 A1 * | 2/2002 | Ukrainczyk et al. | 704/9 |
| 2002/0040363 A1 * | 4/2002 | Wolfman et al. | 707/5 |
| 2002/0059221 A1 * | 5/2002 | Whitehead et al. | 707/5 |
| 2002/0095313 A1 | 7/2002 | Haq | 705/2 |
| 2002/0143824 A1 | 10/2002 | Lee et al. | 707/523 |
| 2002/0169764 A1 | 11/2002 | Kincaid et al. | 707/3 |
| 2003/0046264 A1 | 3/2003 | Kauffman | 707/1 |
| 2003/0061201 A1 | 3/2003 | Grefenstette et al. | 707/3 |
| 2003/0115080 A1 | 6/2003 | Kasravi et al. | 705/1 |
| 2003/0208382 A1 | 11/2003 | Westfall | 705/3 |
| 2003/0233345 A1 | 12/2003 | Perisic et al. | 707/3 |
| 2004/0034524 A1 * | 2/2004 | Rajput et al. | 704/9 |
| 2004/0088158 A1 * | 5/2004 | Sheu et al. | 704/9 |
| 2004/0103075 A1 | 5/2004 | Kim et al. | 707/1 |
| 2004/0139400 A1 | 7/2004 | Allam et al. | 715/526 |
| 2004/0186746 A1 | 9/2004 | Angst et al. | 705/3 |
| 2004/0220895 A1 | 11/2004 | Carus et al. | |
| 2004/0243545 A1 | 12/2004 | Boone et al. | |
| 2004/0243551 A1 | 12/2004 | Boone et al. | |
| 2004/0243552 A1 | 12/2004 | Titemore et al. | |
| 2004/0243614 A1 | 12/2004 | Boone et al. | |
| 2005/0108010 A1 * | 5/2005 | Frankel et al. | 704/235 |
| 2005/0114122 A1 | 5/2005 | Uhrbach et al. | |
| 2005/0120020 A1 | 6/2005 | Carus et al. | |
| 2005/0120300 A1 | 6/2005 | Schwager et al. | |
| 2005/0144184 A1 | 6/2005 | Carus et al. | |
| 2007/0225965 A1 * | 9/2007 | Fallen-Bailey et al. | 704/9 |

OTHER PUBLICATIONS

F. Song et al., A Cognitive Model for the Implementation of Medical Problem Lists, *Proceedings of the First Congress on Computational Medicine, Public Health and Biotechnology*, Austin, Texas, 1994.

F. Song et al., A Graphical Interface to a Semantic Medical Information System, *Karp-95 Proceedings of the Second International Symposium on Knowledge Acquisition*, Representation and Processing, pp. 107-109, Nov. 1994.

*Epic Web Training Manual*, pp. 1-33, May 2002.

B. Hieb, Research Note, NLP Basics for Healthcare, Aug. 16, 2002.

C. Shalizi et al., Pattern Discovery in Time Series, Part I: Theory, Algorithm, Analysis, and Convergence, *Journal of Machine Leaning Research*, 2002.

C. Nevill-Manning et al.,The Development of Holte's 1R Classifier, Department of Computer Science, Proc ANNE '95 pp. 239-242, 1995.

D. Cutting et al., A Practical Part-of-Speech Tagger, Xerox Palo Alto Research Center, 1992.

J. Zavrel et al., Recent Advances in Memory-Based Part-of-Speech Tagging, ILK/Computational Linguistics, 1999.

E. Brill, Some Advances in Transformation-Based Part of Speech Tagging, Spoken Language Systems Group, 1994.

J. Nivre, DAC723: Language Technology Finite State Morphology, Vaxjo University of Mathematics and Systems Engineering, p. 1/11, 2004.

M.. Creutz, Morphology and Finite-State Transducers, Oct. 31, 2001, Chap 3, Jurafsky & Martin, Oct. 2001.

http://www.comp.lancs.ac.uk/computing/research/stemming/general/index.htm printed Jul. 19, 2004, Dec. 2001.

http://www.comp.lancs.ac.uk/computing/research/stemming/general/stemmingerrors.htm printed Jul. 19, 2004, Dec. 2001.

http://www.com.lancs.ac.uk/computing/research/stemming/general/performance.htm printed Jul. 19, 2004, Dec. 2001.

M. Lee et al., Cleansing Data for Mining and Warehousing, Lecture Notes in Computer Science vol. 1677 archive, *Proceedings of the 10th International Conference on Database and Expert Systems Applications*, pp. 751-760, Springer-Verlag, London, 1999.

C. Van Rijsbergen, *Information Retrieval*, 2nd Ed. Ch. 5, Butterworths, London, 1979.

J. Day, Extracting Knowledge from Text Using Learning by Constraint Relaxation (LCR), CSI, www.csi-inc.com/CSI/pdf/jday_icim02.pdf, 2002.

W. Gale et al., Discrimination Decisions for 100,000-Dimensional Spaces, *Current Issues in Computational Linguistics*, pp. 429-450, Kluwer Academic Publishers, 1994.

W. Daelemans et al., TiMBL: Tilburg Memory Based Learner, version 5.0, Reference Guide, *ILK Research Group Technical Report Series No. 04-02 (ILK-0402 )*, ILK Research Group, Tilburg University, Tilburg, Netherlands, 2004.

Case Study: Massachusetts Medical Society http://www.microsoft.com/resources/casestudies/CaseStudy.asp?CaseStudyID=14931 posted Jan. 13, 2004.

W. Braithwaite, Continuity of Care Record (CCR) http://www.hl7.org/library/himss/2004Orlando/ContinuityofCareRecord.pdf, 2004.

C. Waegemann, EHR vs. CCR: What is the difference between the electronic health record and the continuity of care record?, Medical Records Institute, 2004.

Press Release: Kryptiq Announces Support of CCR Initiative and Introduces New Solutions that Enable Information Portability, Accessibility and Clinical System Interoperability, http://www.kryptiq.com/News/PressReleases/27.html, Feb. 17, 2004.

Work Item Summary: WK4363 Standard Specification for the Continuity of Care Record (CCR) http://www.astm.org/cgi-bin/SoftCart.exe/DATABASE.CART/WORKITEMS/WK4363.htm?E+mystore, Mar. 3, 2004.

Continuity of Care Record (CCR): The Concept Paper of the CCR, v. 2.1b, http://www.bhtinfo.com/CCR.Concept%20Paper. 1. 5.doc, 2003.

Continuity of Care Record, American Academy of Family Physicians, http://www.aafp.org/x24962.xml?printxml, Nov. 12, 2003.

Continuity of Care Record (CCR), AAFP Center for Health Information Technology, http://www.centerforhit.org/x201.xml, Aug. 20, 2004.

Core Measures web page, Joint Commission on Accreditation of Healthcare Organizations, http://www.jcaho.org/pms/core+measures/, Feb. 2003.

*Specifications Manual for National Implementation of Hospital Core Measures*, v. 2.0, Joint Commission on Accreditation of Healthcare Organizations, http://www.jcaho.org/pms/core+measures/information+on+final+specifications.htm, Feb. 2003.

Code Information and Education web page, American Medical Association, http://www.ama-assn.org/ama/pub/category/3884.html printed Mar. 22, 2004, Feb. 2003.

Category III CPT Codes, American Medical Association, http://www.ama-assn.org/ama/pub/article/3885-4897.html printed Mar. 22, 2004, Jul. 2001.

ICD-9-CM Preface (FY04), http://ftp.cdc.gov/pub/Health_Statistics/NCHS/Publications/ICD9-CM/2004/Prefac05.RTF, 2004.

*ICD-9-CM Official Guidelines for Coding and Reporting*, effective Oct. 1, 2003.

Q. X. Yang et al., "Faster algorithm of string comparison," *Pattern Analysis and Applications*, vol. 6, No. 1, Apr. 2003: pp. 122-133.

U.S. Appl. No. 10/953,471, filed Sep. 1, 2005, Cote, et al.

U.S. Appl. No. 11/069,203, filed Jul. 27, 2005, Cote, et al.
U.S. Appl. No. 11/007,626, filed Jul. 28, 2005, Cote, et al.
U.S. Appl. No. 10/840,428, filed Oct. 13, 2005, Carus, et al.
U.S. Appl. No. 10/951,281, filed Sep. 22, 2005, Cote, et al.
"Hardware Reference Manual," Release 3 for DOS, revised Jan. 1994, PIKA Technologies, Inc., Ontario, Canada, available at http://www.piketechnologies.com/downloads/legacy/AVA%20B-Series%20Hardware%20Manual.pdf (last accessed Jul. 25, 2005), Jul. 1989.

"Customizing D/41 Call Analysis," date unknown, Intel Corp., Santa Clara, California, available at http://resource.intel.com/telecom/support/appnotes/custd41d.htm (last accessed Jul. 25, 2005), Sep. 2002.

* cited by examiner

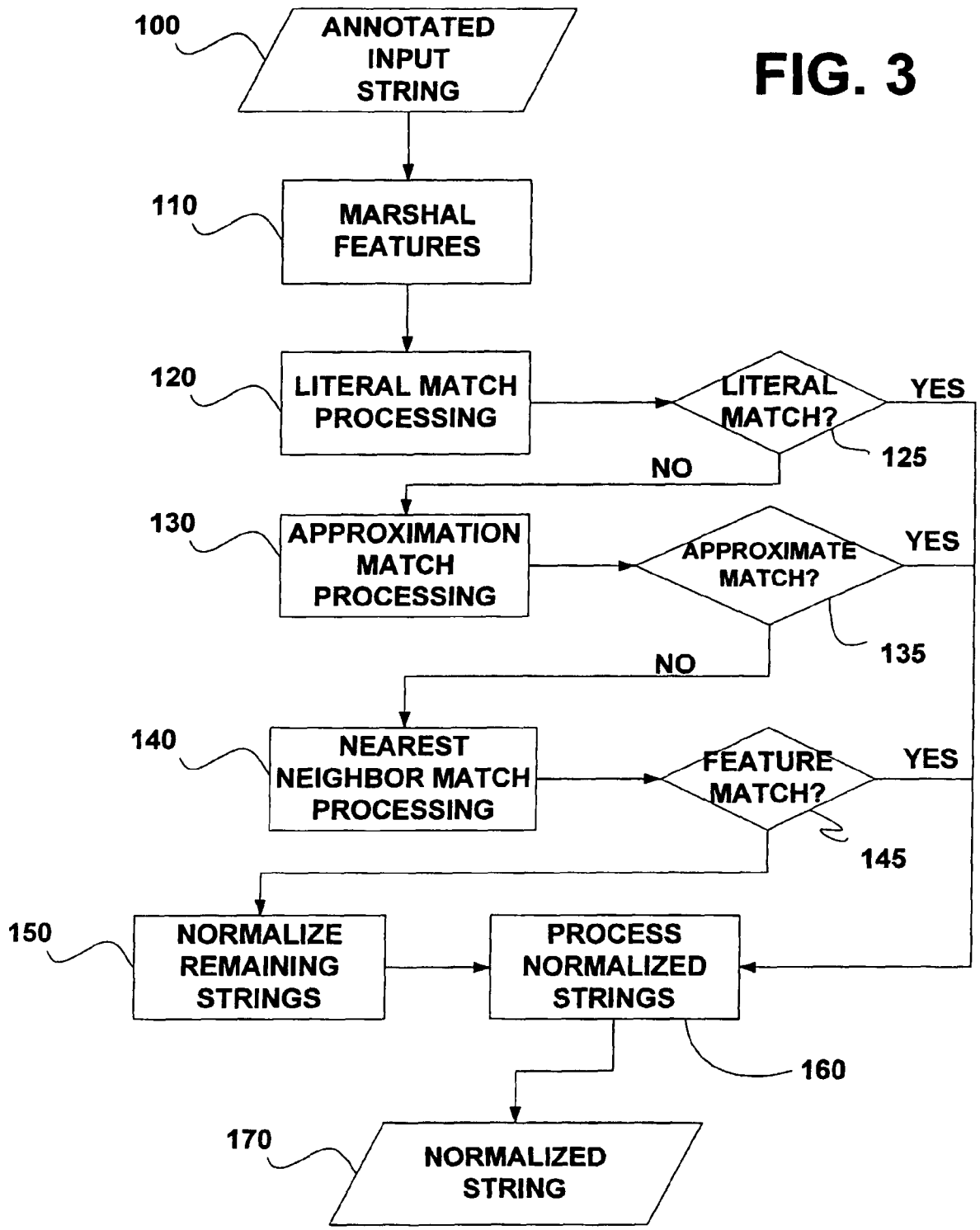

SYSTEM AND METHOD FOR NORMALIZATION OF A STRING OF WORDS

CROSS-REFERENCE TO RELATED APPLICATIONS

This application claims the benefit of priority of U.S. Provisional Patent Application No. 60/547,797, entitled "A SYSTEM AND METHOD FOR NORMALIZATION OF A STRING OF WORDS," filed Feb. 27, 2004, which is hereby incorporated by reference in its entirety.

This application relates to co-pending U.S. patent application Ser. No. 10/447,290, entitled "SYSTEM AND METHODS UTILIZING NATURAL LANGUAGE PATIENT RECORDS," filed on May 29, 2003; co-pending U.S. patent application Ser. No. 10/413,405, entitled "SYSTEMS AND METHODS FOR CODING INFORMATION," filed Apr. 15, 2003; co-pending U.S. patent application Ser. No. 10/448,320, entitled "METHOD, SYSTEM, AND APPARATUS FOR DATA REUSE," filed on May 30, 2003; co-pending U.S. patent application Ser. No. 10/787,889, entitled "SYSTEM, METHOD AND APPARATUS FOR PREDICTION USING MINIMAL AFFIX PATTERNS," filed on Feb. 27, 2004; co-pending U.S. patent application Ser. No. 10/448,317, entitled "METHOD, SYSTEM, AND APPARATUS FOR VALIDATION," filed on May 30, 2003; co-pending U.S. patent application Ser. No. 10/448,325, entitled "METHOD, SYSTEM, AND APPARATUS FOR VIEWING DATA," filed on May 30, 2003; co-pending U.S. patent application Ser. No. 10/953,448, entitled "SYSTEM AND METHOD FOR DOCUMENT SECTION SEGMENTATIONS," filed on Sep. 30, 2004; co-pending U.S. patent application Ser. No. 10/953,471, entitled "SYSTEM AND METHOD FOR MODIFYING A LANGUAGE MODEL AND POST-PROCESSOR INFORMATION," filed on Sep. 29, 2004; co-pending U.S. patent application Ser. No. 10/951,291, entitled "SYSTEM AND METHOD FOR CUSTOMIZING SPEECH RECOGNITION INPUT AND OUTPUT," filed on Sep. 27, 2004; co-pending U.S. patent application Ser. No. 10/953,474, entitled "SYSTEM AND METHOD FOR POST PROCESSING SPEECH RECOGNITION OUTPUT," filed on Sep. 29, 2004; co-pending U.S. patent application Ser. No. 10/951,281, entitled "METHOD, SYSTEM AND APPARATUS FOR REPAIRING AUDIO RECORDINGS," filed on Sep. 27, 2004; co-pending U.S. patent application Ser. No. 11/069,203, entitled "SYSTEM AND METHOD FOR GENERATING A PHASE PRONUNCIATION," filed on Feb. 28, 2005; co-pending U.S. patent application Ser. No. 11/007,626, entitled "SYSTEM AND METHOD FOR ACCENTED MODIFICATION OF A LANGUAGE MODEL," filed on Dec. 7, 2004; co-pending U.S. patent application Ser. No. 10/948,625, entitled "METHOD, SYSTEM, AND APPARATUS FOR ASSEMBLY, TRANSPORT AND DISPLAY OF CLINICAL DATA," filed on Sep. 23, 2004; and co-pending U.S. patent application Ser. No. 10/840,428, entitled "CATEGORIZATION OF INFORMATION USING NATURAL LANGUAGE PROCESSING AND PREDEFINED TEMPLATES," filed on Sep. 23, 2004, all of which are hereby incorporated by reference in their entirety.

BACKGROUND OF THE INVENTION

The present invention relates generally to a system and method for categorization of strings of words. More specifically, the present invention relates to a system and method for normalizing a string of words for use in a system for categorization of words in a predetermined categorization scheme.

There are a number of systems capable of analyzing a section of text to determine the significance of that section of text. Some exemplary fields of information classification and analysis include the identification of names of people, their roles or positions within various organizations, product names, and names of organizations such as information extraction systems developed for the DARPA and NIST MUC experiments. On a very basic level, the analysis of text typically involves two steps. First, the relevant string of text, or the string of interest should be identified. This may require some form of isolation from other strings of text or other text within a given string. Secondly, once the bounds of the text of interest have been determined, the text should be characterized and tagged with labels. Some algorithms may combine these two steps into a single step. Traditionally, data has been classified on a number of different levels including complete texts, sections of documents, paragraphs, single sentences, and even strings of words within a sentence.

Traditional systems utilize broad categories when classifying information and do not permit the classification of words, or strings of words into the categories of complex ontologies or nomenclatures. In fact, traditional systems may prove unwieldy or unmanageable when applied to several thousand or more distinctions, as would be required to characterize text within even a moderately complex ontology or nomenclature. Prior classification schemes are, therefore, comparatively high-level and, may produce ineffective classification of information for particular applications.

One example of nomenclature that is very complex in nature is found in medicine and medical diagnosis. For example, a medical diagnosis may include information related to the intensity of a particular malady, the anatomical site of an infliction or complications relating to the diagnosis. One physician within the medical profession may state a diagnosis in way that is not necessarily identical to the way another physician will state the same diagnosis. This may be due to, for example, a difference in word order, different complications associated with a particular diagnosis, the diagnosis may be associated with a slightly different part of the anatomy, or a diagnosis may indicate a medical problem having a range of different intensities. This list is not intended to be exhaustive, but is illustrative of the number of different reasons why an identical diagnosis can be stated in a number of forms. For a given lexicon of medical problems, there may be millions or even billions of ways to express diagnoses of medical problems.

One example of such a complex hierarchically-organized nomenclature is the SNOMED CT (Systematized Nomenclature of Medicine Clinical Terms) nomenclature. SNOMED is a common index or dictionary against which data can be encoded, stored, and referenced. The SNOMED CT nomenclature includes hundreds of thousands of differing categories of medical diagnoses based on the large number of different concepts within the medical field. A much smaller subset of the SNOMED CT, the Dictaphone SNOMED CT Clinical Subset, includes only about 7,000 of the approximately 100,000 disease and findings categories that the entire SNOMED CT ontology includes.

In the hospital or clinical setting, dictation of diagnoses and patient records is common. Once dictated, the speech can be converted directly into text either manually or with speech recognition systems. Due to differences in spoken medical diagnoses, however, systems may not properly recognize or classify a particular diagnosis. Therefore, a system and method for recognizing and classifying text such as a medical diagnosis will preferably be configured to accommodate a large degree of variability within the input text strings. Such variability may be due to, for example, dictation by medical professionals including professionals in different departments of a hospital, professionals in different hospitals, professionals having different specialties, professionals having different backgrounds, dictation at different time periods, and dictation in different contexts.

Therefore, what is needed is a system and a method for classifying words and strings of words into categories of complex ontologies or nomenclatures, such as would exist, in for example, the SNOMED CT nomenclature. The present invention seeks to address this and other potential shortcomings of prior art systems and methods when applied to complex nomenclatures, including, for example, complex hierarchically organized nomenclatures.

SUMMARY OF THE INVENTION

In light of the above-identified deficiencies of contemporary systems, it is thus an object of the present invention to provide a system and method to addresses some of the problems associated with classifying strings of words in complex, hierarchically-organized nomenclatures.

In a first aspect, the present invention includes a method for the adaptive categorization of words in a predetermined categorization scheme, including the steps of receiving a string of text, tagging the string of text, and normalizing the string of text. Once the string of text has been normalized, the normalized string of text may be compared to a plurality of sequences of text within the predetermined categorization scheme. If the normalized string of text substantially matches at least one of the plurality of sequences of text in the predetermined categorization scheme, data can be output. The data can be associated with the normalized string of text. If the normalized string of text does not substantially match at least one of the plurality of the sequences of text within the predetermined categorization schemes, the string of text may not be classified within the predetermined classification scheme.

In a second aspect, the present invention includes a method for categorization of strings by receiving a string of words. The received string of words can be compared to a literal index. The literal index may contain predetermined text sequences. A determination may be made as to whether the string of text matches at least one of the plurality of predetermined text sequences.

If a substantial match for the received string of words is not found in the literal index, the individual word forms of the input string of text may be reduced to at least one baseform. The baseform may then be sorted. The sorted sequence of baseforms may then be compared to a number of predetermined baseform sequences. These predetermined baseform sequences may be stored in, for example, a baseform index. A score may be computed based on the comparison of the baseforms with the predetermined baseform sequences in the baseform index. If this score exceeds a predetermined threshold, then feedback may be produced.

If there are no baseforms that exceed the predetermined threshold score, a feature transformation may be computed for the input string. The feature transformations resulting from this computation may be compared to a number of predetermined feature sets. Based on this comparison, a score may be determined for at least some of the predetermined feature sequences and a hit list may be generated based on these scored feature transformations. The hit list may include a list of candidate sequence matches based on the input string. In the event that no predetermined feature sequence matches are found based on the input string, an indication may be output indicating that the input string produced no matches.

In a third aspect, the present invention includes a system normalizing a string of words for use in a predetermined categorization scheme including a computer having a computer code mechanism programmed to receive a string of text, tag the string of text, create a normalized string of text and compare the normalized string of text to a plurality of sequences of text within the predetermined categorization scheme. The system also includes a means for matching at least one normalized string of text to at least one of the plurality of the sequences of text in the predetermined categorization scheme, a means for outputting data associated with the normalized string of text based on the comparison of the normalized string of text with the sequences of text within the predetermined categorization scheme, and a means for matching for classifying the string of text within the predetermined categorization scheme.

In a fourth aspect, the present invention includes an apparatus for normalizing a string of words for use in a predetermined categorization scheme including a computer having a computer code mechanism programmed to receive an input string of text, compare the input string to a literal index, where the literal index includes a plurality of predetermined text sequences, and determine if the string of text matches at least one of the plurality of predetermined text sequences within the literal index. In some embodiments the apparatus includes a means for determining a baseform transform of the input string, where the baseform transform includes at least one baseform associated with the input string. In some embodiments the apparatus also includes a means for preparing a sorted version of the baseform transform, a means for comparing the at least one baseform to a baseform index, where the baseform index includes a plurality of predetermined baseform sequences and a means for determining a score for each of the plurality of predetermined baseform sequences that substantially match the at least one baseform and outputting feedback for any baseforms that exceed a predetermined threshold score. In still other embodiments the apparatus may include a means for determining a feature transformation of the input string where the feature transform includes at least one feature associated with the input string, a means for comparing the at least one feature to a feature index where the feature index includes a plurality of predetermined feature sequences, and a means for determining a score for each of the plurality of predetermined feature sequences that substantially match the at least one feature. In yet other embodiments the apparatus may include a means for outputting a hit list of candidate sequence matches based on the input string. In another embodiment the apparatus includes a means for outputting an indication that no predetermined text sequences were found within the predetermined categorization scheme.

BRIEF DESCRIPTION OF THE DRAWINGS

While the specification concludes with claims particularly pointing out and distinctly claiming the invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures wherein:

FIG. 3 shows another logic flow diagram according to another embodiment of the invention;

DETAILED DESCRIPTION OF THE PREFERRED EMBODIMENTS

Figure 1:
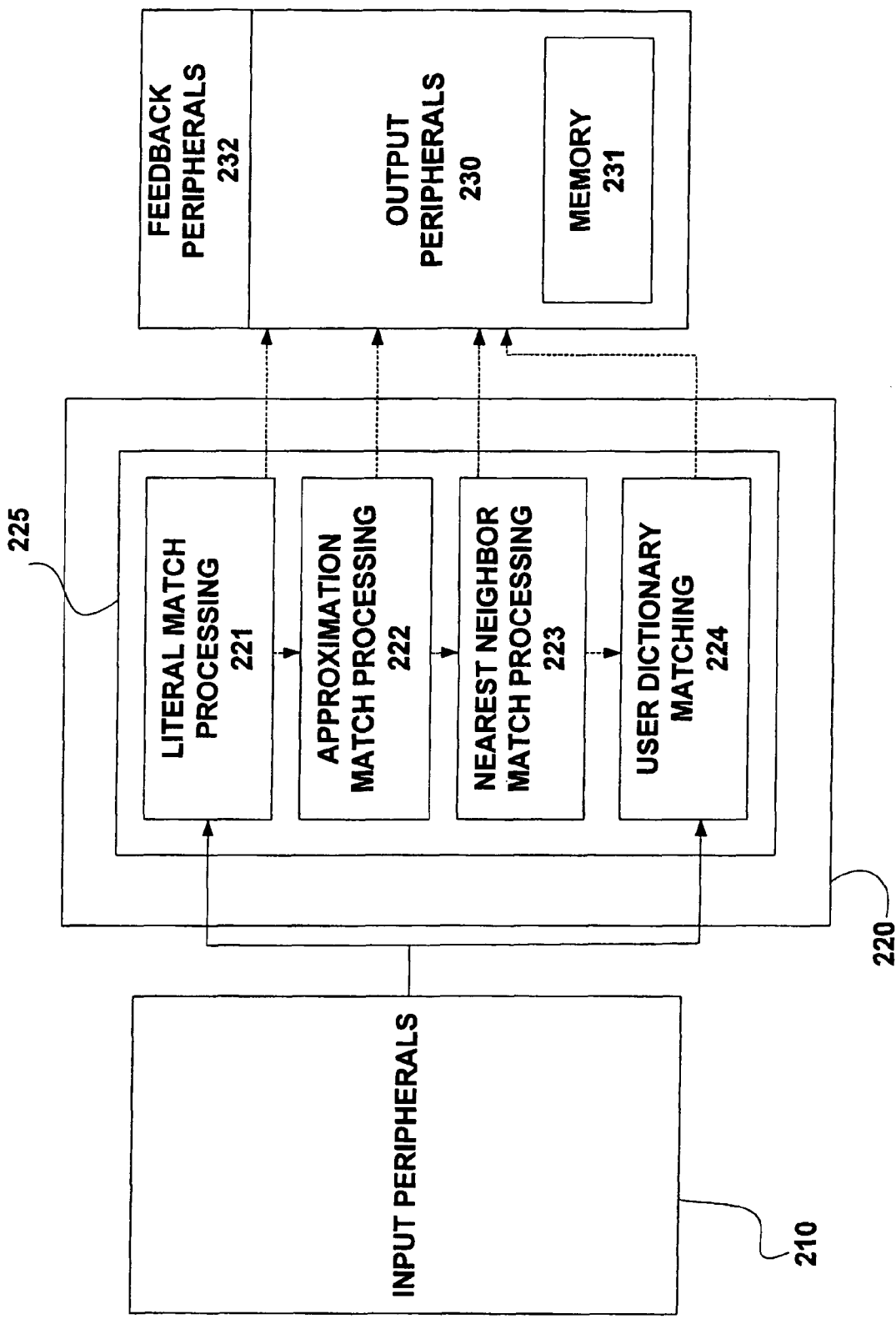
FIG. 1 shows a system and software architecture according to an embodiment of the invention.

The present disclosure will now be described more fully with reference to the Figures in which embodiments of the present invention are shown. The subject matter of this disclosure may, however, be embodied in many different forms and should not be construed as being limited to the embodiments set forth herein.

A predetermined categorization scheme may be a lexicon or standardized representation of a particular ontology or nomenclature. The SNOMED CT nomenclature is one example of a predetermined categorization scheme. The SNOMED nomenclature is a rich and well-regarded description of medical concepts and their relationships. One benefit of a predetermined categorization scheme is that the prerecorded expressions are built up in a manner similar to how they might be said by, for example, a medical practitioner. In one embodiment, the SNOMED CT nomenclature was modified considering the competing interests of providing adequate variety in the overall descriptions and the ability to accurately identify strings of text that are associated with these descriptions.

In one embodiment, the predetermined categorization scheme is a dictionary. A dictionary as used in connection with the invention may include a number of different features including: entries, entry numbers associated with a particular entry location table; a literal index; a baseform index; a semantic category priority table; a feature weight table; and an entry frequency table. Some or all of these features may be used depending on the complexity of the nomenclature and the normalization required.

Within a dictionary, there may be tens of thousands of entries. Each entry may correspond to a unique string of characters. In one embodiment, the string may name or define a medical problem. Entries can have a variable number of characters, and therefore, the amount of data associated with a particular string of text may differ from one string to the next. These entries may be represented, for example, in a markup language. In one embodiment, these entries are represented as XML documents. Each XML document may include the following data: a string; an absolute frequency of that string in the corpus of the dictionary; a code associated with the string; the baseform transform of the string; and the feature transform of the string. If an entry contains more than one code associated with the entry, there may be an additional entry field indicating the preferred code associated with the entry. A sample dictionary entry using the Dictaphone SNOMED CT Clinical Subset may look like the following:

```
<entry>
    <String val ="acanthosis nigricans"/>
    <codes val="254666005,95320005"/>
    <preferred val="95320005"/>
    <baseform val ="acanthosis nigrica"/>
    <features val="PRIMARY.'acanthosis' PRIMARY.'nigrica'"/>
</entry>
```

The string may include data tending to describe a particular term. For example, using the Dictaphone SNOMED CT Clinical Subset, the string may be the name or a description of a medical problem. The strings may come from the SNOMED CT data, and actual medical documents. Any reliable source of information may provide strings. In the dictionary, strings may be modified to a small degree relative to how they may appear in, for example, a document, or another original source. These modifications may include the removal of capitalizations, stripping leading and trailing white space, changing all sequences of internal white space to single spaced, replacing some punctuation characters with single spaces, replacing some punctuation characters with single spaces, and stripping other kinds of punctuation altogether. Because the format of these dictionary strings is similar, the first step in the normalization algorithm is to perform the same modifications or normalizations on the input strings as were performed on the entries themselves.

Codes may include an identifier associated with the term within the dictionary. They may be used for purposes such as cataloging terms in a hierarchy, for example. In one embodiment, medical problems may be coded with a selection of codes from the SNOMED CT Clinical Subset. The Clinical Subset contains codes selected form SNOMED CT on the basis of clinical frequency and relevance.

Preferred codes may become necessary when input strings are associated with more than one code. For the strings having more than one code associated with the string, a particular code may be marked as a preferred code. This preferred code may be used to sort returns from the algorithm. When a dictionary entry that has multiple codes is the most similar to an input problem, the algorithm may be configured to put the preferred code at the top of the list, as will be described in more detail below.

The baseform transform may be computed from the literal string. In the baseform transform, noise words (i.e., non-content words) may be removed, and the remaining words may be stemmed using de-derivation and un-inflection. In one embodiment, de-derivation may be performed prior to un-inflection. Alternatively, un-inflection may be performed prior to de-derivation. The stemmed terms within the baseform transform may appear in the same relative order that they did in the original string.

The feature transform may be computed from an analysis of the literal string. The tagger may distinguish words so as to place them into sets of semantic categories. For example, the problem tagger may formulate the strings after tagging in the following form: CATEGORY.word, where category identifies the semantic category of the word. For some words or phrases, in addition to these semantic features, "hypernym features" may be generated. For example, when one of a number of words related to cancer is found in a problem name, such as, for example, carcinoma and adenocarcinoma, the tagger may create both the word-based feature and the hypernym feature. The word-based feature may be formatted to resemble PRIMARY.'cancer word' and the hypernym feature may resemble PRIMARY.NEOPLASM.'cancer word'. In XML code, this may be written as follows:

```
<entry>
    <codes val="95324001"/>
    <string val="acantholytic dyskeratoic epidermal nevus"/>
    <baseform val="avantholysis dyskeratosis epidermis nevoid"/>
    <features val="DPT_MODIFIER.'acantholysis'
    PRIMARY.'epidermis'
PRIMARY.'nevoid.'PRIMARY NEOPLASM
SECONDARY.'dyskeratosis'"/>
</entry>
```

Each entry within the particular predetermined classification scheme may be assigned a unique entry number. This may be a number 1 to N, where N is the total number of entries found in the dictionary. Since entries may be variable length, a table that maps entry numbers to their locations in the entry data may be required. This may allow the actual entry data to be retrieved efficiently, once the entry number has been determined.

The literal index may include a series of numbers corresponding to a problem name or a description. As discussed in further detail below, this index may be used in the literal match processing within the normalization algorithm, which may attempt to find an input string of text literally within the predetermined classification scheme.

The baseforms index may include a vector of entry numbers for entries containing that baseform in the baseform transform. For example, every time a particular baseform appears in the baseform index, a code may be produced and added to the vector of codes associated with the particular baseform of the input string. For example, in one embodiment of the invention using the Dictaphone SNOMED CT Clinical Subset, the term 'nigrica' may occur in its baseform for eleven different dictionary entries. Thus, the results would appear as follows: nigrica→804 805 2144 7882 23974 30833 35557 37663 37664 37670 40282. The baseform index may be used, for example, in the approximation processing step, as described below.

The features index may include the vector entries for each feature occurring within the dictionary. Numbers for entries containing a particular dictionary entry may be associated with a particular feature. For example, PRIMARY.'acanthosis'→803 804 805 806 2144 7882 23974 30833 3557. Thus, as shown in this example, the feature "PRIMARY.'acanthosis'" occurs in the feature transform index for nine different dictionary entries. This index may be used in the nearest—neighbor matching algorithm, which uses the feature transforms to do approximate matching over semantic features. By indexing the features, it is possible to quickly narrow down the entries within the predetermined classification scheme that have any possibility of scoring Well against the input.

Semantic categories are prefixes of features. For example, in the following expression ANATOMY-DEVICE.'prosthesis', the semantic category is "ANATOMY-DEVICE." For each semantic category used in features, the priority table may include an integer relative priority rank of that category. This table may be used to identify the core concepts found within input strings, as discussed with respect to some embodiments of nearest neighbor processing, below.

The feature weight table may include a floating-point number for each feature in the predetermined classification scheme. This floating-point number may be between, for example, (0,1]. This floating-point number may reflect the information gain ratio associated with the feature. The information gain ratio is a figure of merit connoting how well a particular feature discriminates among entries.

Some computations performed by the normalization algorithm may use the frequency of an entry string within the predetermined classification scheme. These frequencies may be derived from a large corpus of medical documents. These frequencies may be stored in a table separate from the entries themselves, so that the entries do not have to be retrieved in order to get a particular entry frequency. Alternatively, the frequencies may be stored with the entries. When given an entry number, the table may be referenced to provide the absolute frequency of the entry's string. As an integer value, this may, in some instances, be more efficient and convenient to use for some purposes than the floating-point relative frequency. The sum of all frequencies may be available from this table (but may require a special key), so that the normalizer may compute the relative frequency of any input string, if required.

Referring now to FIG. 1, there is shown a structural and software architecture according to an embodiment of the invention. Structural and software architecture 200 can include input peripherals 210, processor 220, and output peripherals 230. Input peripherals 210 can permit a user to input certain data, for example, input peripherals may include a keyboard, a computer mouse, a microphone or any other input peripheral device that may permit the input of strings of text into the processor 220. Processor 220 can be configured to perform a number of normalization and classification steps stored within, for example, a software module 225 including a normalization algorithm. Software module 225 can include submodules for literal match processing 221, approximation match processing 222, nearest neighbor match processing 223, and user dictionary match processing 225. Strings of text that may be input via input peripherals 210 may be processed in each of these submodules. In some embodiments the user dictionary match processing 225 is optional. Depending on the ability of the literal match processing 221 and approximation match processing 222 to identify matches for an input string of text, the outputting of a match may occur at a different stage in the processing. The normalization algorithm can be configured such that an early exit from the algorithm is preferred. Therefore, outputs from each of the submodules 221-224 are indicated by dashed lines.

Figure 2:
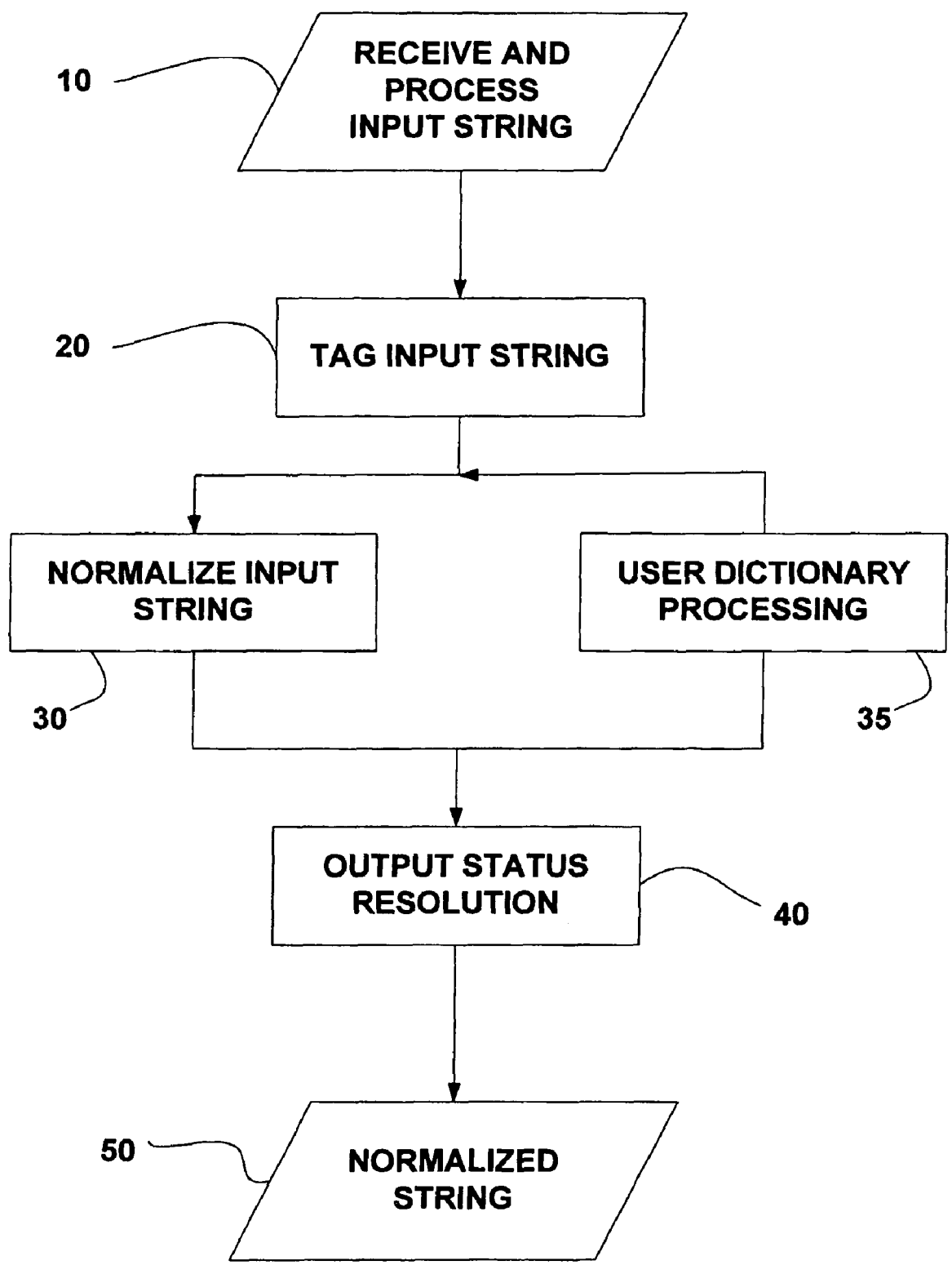
FIG. 2 shows a logic flow diagram according to one embodiment of the invention.

Referring now to FIG. 2, there is shown a logic flow diagram according to one embodiment of the invention. Once a string of words is received, the words can be preprocessed, step 10. Preprocessing may be accomplished by a means of preparing the input string for data extraction, and can include, for example, removing all capitalizations and removing punctuation. Alternatively, this step may be performed in connection with literal match processing, discussed below.

After the input string has been preprocessed, the preprocessed string may be input into an input string tagger, step 20. Input string tagging 20 can include, for example, the identification of candidate medical problems. In one embodiment, input string tagger can be configured to identify candidate medical problems and can annotate strings of words associated with candidate medical problems with labels indicating the start and end positions of the candidate medical problem and the semantic composition of the candidate medical problem. In one embodiment, input strings can be annotated with, for example, out-of-line XML mark-up. Various other mark-up languages or annotation means can be used to annotate the input strings for further processing.

An example of tagging and how it works to annotate a particular input string of text is as follows. An exemplary input sting may be "he was admitted for acute pulmonary edema." The medical problem tagger can identify the relevant medical problem and tag the medical problem accordingly. For example, the word "acute" can be associated with the semantic label "DPT-ACUITY," the word "pulmonary" can be tagged with the semantic labels "ANATOMY::ANATOMICAL ADJECTIVE" and the word "edema" can be tagged, for example, with the semantic label "DISEASEOFBODYPART." As will be described in more detail below, the input string tagger may ignore irrelevant noise words (i.e., non-content words). The semantic labels are merely exemplary, and a myriad of different semantic labels may be used to annotate an input string depending on the predetermined classification scheme used, and the desired labels for each of the semantic categories.

Once the input string has been annotated, it can be further processed. Other information (i.e., noise or other non-content words) that may have been included in the input string need not be further processed, and can be ignored. Therefore, the analysis of the input string can be limited to the relevant text of interest (e.g., an input medical problem) within the input string and the annotations of the input string applied by the tagger. This can decrease the overall processing time associated with running the algorithm. The annotated input string may then be processed by the normalizer, step 30. The normalization step 30 can take an input string identified by the tagger, along with other information associated with the string, such as, for example, the tagger's analysis of the semantic categories for words in the string, and can output candidate normalizations for the input string, as will be described in further detail below. In one embodiment, the annotated input string can be an annotated candidate medical problem, and the normalization step 30 can output candidate medical problem normalizations. The normalization step 30 can include a three-stage normalization process. The three-stage normalization process 30 can include a literal match processing stage, an approximation match processing stage and a nearest neighbor match processing stage, which may use, for example, k-nearest neighbor pattern matching to identify possible matches for the input string of text. The literal matching stage may substantially identify exact matches; the approximation match processing stage may identify one or more approximate matches. The nearest neighbor match processing stage may require thousands of comparisons between the input string and the feature index, while the literal and approximation match processing stages may require substantially fewer comparisons to be made between the input string and the literal and baseform index, respectively.

A method of normalizing an input string, including, for example, a medical problem, can also include a step including user dictionary processing, step 35. User dictionary processing 35 can permit a user to define specific input strings, for example, a common medical problem. User dictionary processing 35 can be run in parallel with the input string normalization illustrated in step 30. Alternatively, user dictionary processing can be run in series with normalization step 30, with the user dictionary being prior to the normalization to permit early exit from the algorithm. By permitting a user to define certain strings, not only can corrections or adjustments be made to the proper classification of the user's strings, but processing time may be reduced when the input string literally matches a user-defined string.

After normalization of the input string, step 30, and/or user dictionary processing, step 35, the output status resolution can be output, step 40. Output status resolution relates to the significance or relevance of the identified unit of information in the target document (i.e., the input string). For example, negated medical problems or medical problems from past medical problems may play a different role in characterizing the medical status of a patient. A negated medical problem may be identified by, for example, a negation module that identifies the presence of a negation and the scope of the negation (i.e., the terms which are negated). In one embodiment, past medical history may be identified by section headings within the predetermined classification scheme. One reason to perform the output status resolution, step 40, is to reconcile any potential conflicts between medical problems (or other string matches) that were tagged and categorized in the normalization step 30, and those that were tagged and categorized by user dictionary processing step 35.

If a conflict between, for example, a medical problem that was matched by the normalization step 30 and those matched by user dictionary processing step 35 is found, the algorithm can demote the medical problems that were matched by the normalization step 30 and promote those matched by the user dictionary processing step 35. In one exemplary embodiment, the algorithm can continue parallel processing of both strings, while favoring the medical problem matched by user dictionary processing step 35. In another embodiment, the algorithm can terminate the medical problem matched by the normalization step 30. In yet another embodiment, algorithm can prompt a user to determine if both medical problems should be processed, or if one matched medical problem should be terminated in favor of another matched medical problem.

As discussed above, performing output status resolution, step 40, can also apply a prediction in scope. Thus, input strings, including matches of the input string identified by user dictionary processing step 35, can be placed into categories. In one embodiment of the invention where the input string is a medical problem, such categories can include, but are not limited to, current problems, historical problems and the like. Any number of categories are possible. This information may be stored in a database archive or presented as out-of-line XML markup. This information may then permit a user to select or differentially present, for example, medical problems based on their output status categories.

After performing the output status resolution, the matches associated with the input string determined in normalization step 30 and/or user dictionary processing step 35 can be output, step 50. The algorithm can output one or more predetermined entries associated with the input string to the user, step 50, using, for example, visual or audible devices. Such devices include, for example, a computer monitor, speakers, a liquid crystal display ("LCD"), speakers, or other means for providing feedback to a user.

Referring now to FIG. 3, there is shown a logic flow diagram according to another embodiment of the invention. FIG. 3 illustrates in more detail the normalization that takes place in, for example, step 30 illustrated in FIG. 2. As illustrated in FIG. 3, the normalization process can be configured to seek an early exit from the algorithm. For example, if a match is found in the literal match processing stage, then the algorithm does not proceed to the approximation match processing stage. Likewise, if the candidate medical problem matches in the approximation match processing stage, then the algorithm does not proceed to the nearest neighbor match processing stage.

An annotated input string can be received into the algorithm. In one embodiment of the invention, the input string can be an input medical problem. As discussed with respect to FIG. 2, a tagger may annotate the input string by marking the beginning of the relevant portion of the input string, for example, a medical problem within an input string, and the end of the relevant portion of the input string with an appropriate tag. After the annotated input string is received into the algorithm, step 100, the features of the input string are marshaled. Marshalling may include identifying individual features associated with the input string. Once these features are identified, additional features may be generated using the individual features. Marshalling may include the generation of combinational features.

After the features are marshalled 110, the annotated input string can be input into literal matching step 120 of the algorithm. Literal matching step 120 can be purely lexical. Literal matching step 120 can include a minimal amount of processing of the input string. This processing can include, for example, removal of unnecessary capitalization and removal of punctuation. In some embodiments, additional normalizations can be used, such as, for example, removal of excess white space. The removal of excess white space can reduce the white space to single inter-token white space with no leading or trailing white space. Literal matching step 120 substantially compares the input string with an index of entries, referred to herein as a literal index. The index can include a number of predetermined word sequences. The input medical problem string can be compared to the predetermined word sequences stored in the literal index to determine if there is a literal match, step 125.

When literal matching stage 120 finds one or more relevant literal matches, the entry number and entry location can be resolved. The codes associated with elements in the entry can be read. In one embodiment of the invention, if more than one code has been resolved, a preferred element code can be read. In an alternative embodiment, all elements and associated codes can be read. In an alternative embodiment, a predetermined subset of codes and elements can be read from the list of literal matches.

After the codes and elements are read, as appropriate, scoring in the literal matching step 120 can be done by, for example, comparison of terms for overlap, or alternatively by one-to-one string correspondence. The threshold of acceptability of the literal match processing step 120 can be relatively high. Therefore, any literal matches that are found for the input medical problem can be ranked and sorted in accordance with the number of matching tokens. Results that matched the input medical problem exactly may be output. Alternatively, match results that match the input medical problem above a threshold value, for example, 98% match (corresponding to a score of 0.98), will be output. Any threshold may be set depending on the nature of the nomenclature that is being matched to. In the medical profession, a high degree of accuracy in the match may be necessary, and therefore, the literal match processing 120 can be configured to output only exact matches for a given input medical problem. If an exact match is produced, the list can be returned and the algorithm can exit. If literal match processing 120 does not achieve a lower-bound threshold, which can be fixed at 1.0 (corresponding to a 100% match), the algorithm can proceed to approximation match processing step 130.

If there is a match between the input string and at least one of the predetermined word sequences, then remaining input strings can be normalized, step, 150; the normalized input strings can be processed, step 160; and the categories of the normalized strings can be output 170 to, for example, a user. The remaining strings may be processed in the aforementioned manner.

In some embodiments of the invention, if at least one candidate medical problem matches a predetermined word or word sequence stored within the literal matching index, an associated clinical subset code can be retrieved from SNOMED CT. By using the SNOMED CT nomenclature, the system can classify and map clinical data from numerous sources for easy retrieval and future use, in a standardized and consistent format. In some embodiments, it may be necessary to permit the retrieval of more than one exact match because it may be necessary to retrieve more than one code for a given string. In some instances, SNOMED CT may provide more than one code for a given input string. The code output from the algorithm may also be used to retrieve SNOMED CT preferred descriptions or other elements for presenting to end-users. Alternatively, the returned codes may be used to further refine a search for a match within the SNOMED CT diagnosis hierarchy.

Literal matching step 120 may use both the comparison of terms and a method of one-to-one string correspondence. Any simple string comparison algorithm may be used with the literal matching step 120. Alternatively, a complex pattern matcher may be used in connection with the literal matching step 120, potentially at the expense of processing speed.

If a literal match is not found in step 125, the input medical problem string may be further processed in an approximation match processing stage, step 130. Similar to the literal stage processing 120, approximation match processing 130 may also be purely lexical. Approximation match processing 120 includes steps for approximate string matching. In approximation processing step 130, two processes can occur: (1) literal match normalization; and (2) the baseforms of the text associated with the input string can be computed.

Figure 4A:
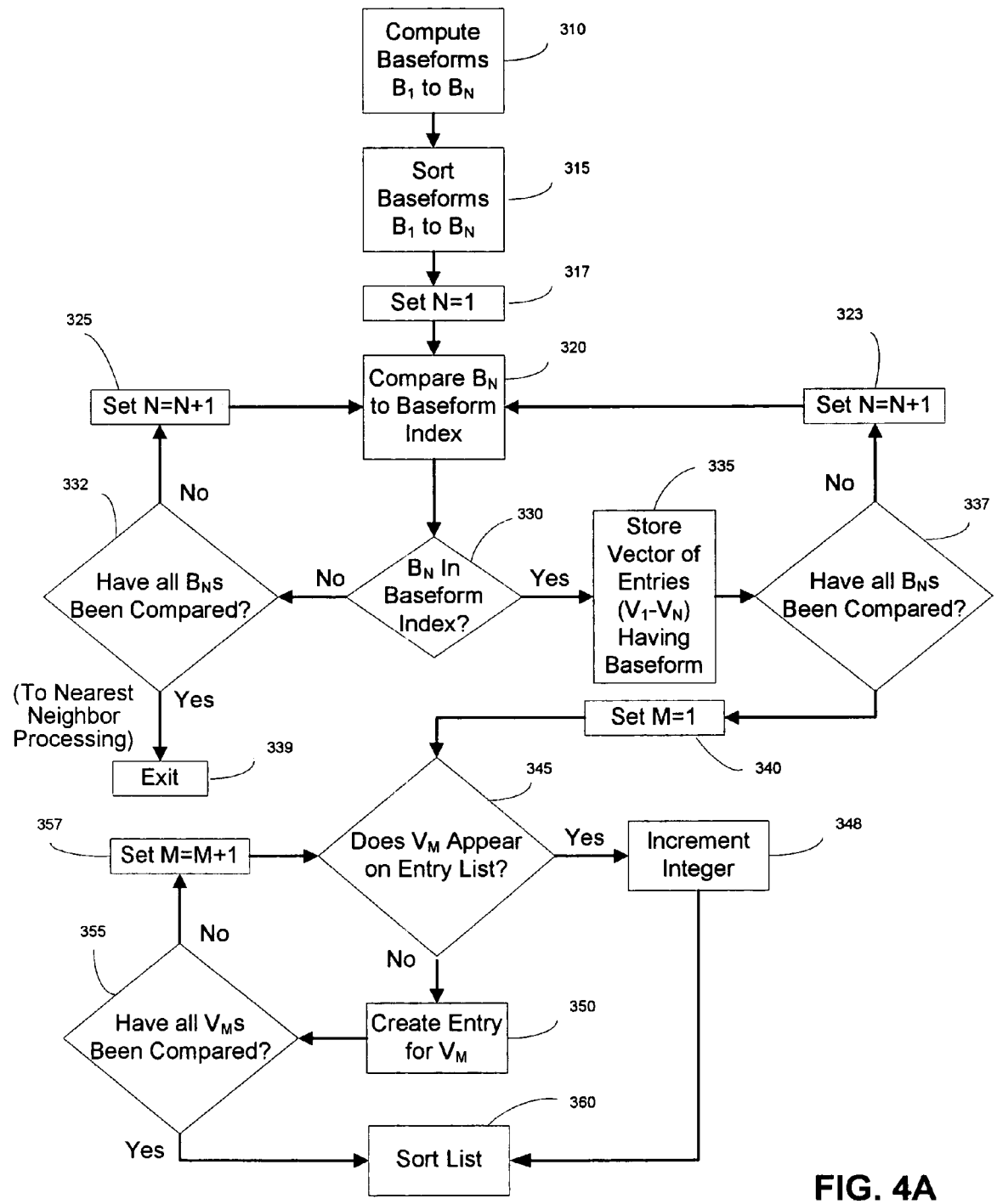
FIGS. 4A-4C show a logic flow diagram detailing a process as shown in FIG. 1 according to one embodiment of the invention.
Figure 4B:
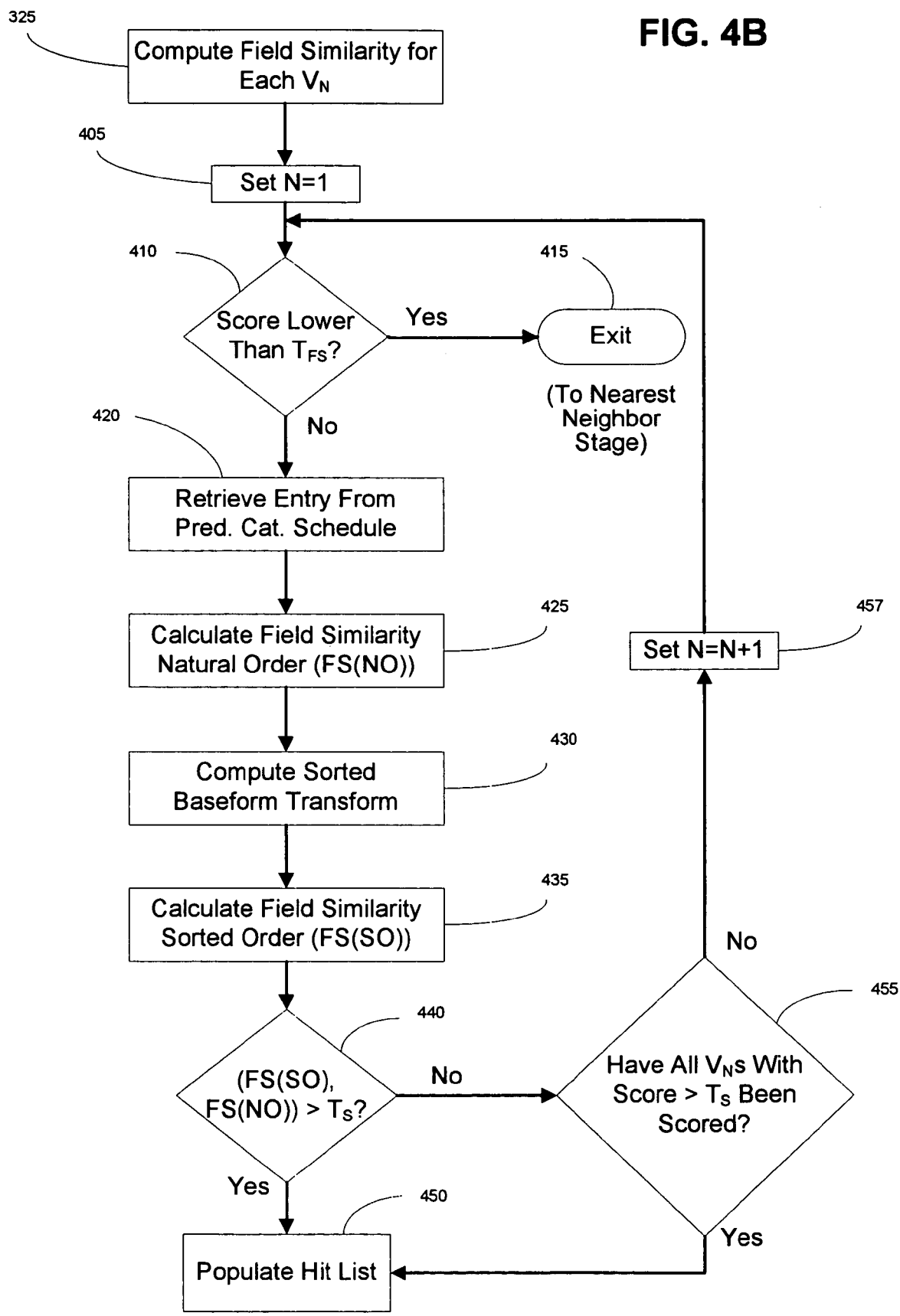
Figure 4C:
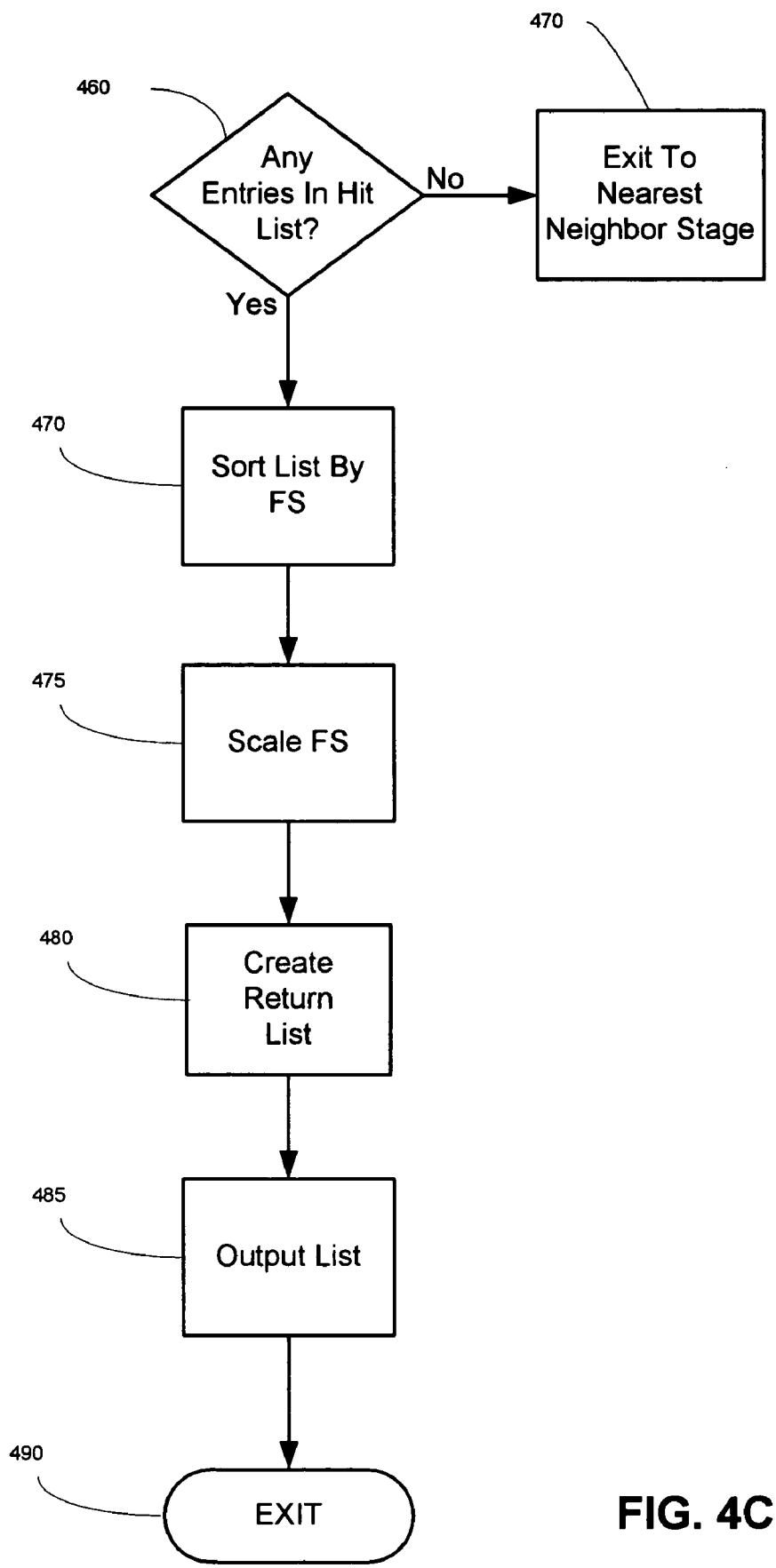

Approximation processing step 130, shown in detail in FIGS. 4A, 4B and 4C, including literal match normalization may normalize the input string in substantially the same way that the input string was normalized in literal stage processing step 120. For example, capitalization and punctuation may be removed. Additionally, white-space may be reduced to single intra-token white space.

Approximation processing step 130 may also include computing the baseform of the tagged input string, which can be, for example, a medical problem. Baseforms may be computed as shown in step 310 using either inflectional and derivational stemming, or both inflectional and derivational stemming. Inflectional stemming includes reduction of a word to its base form. A simple example of inflectional stemming includes the mapping of the terms "found" and "finds" to the baseform "find." In contrast, derivational stemming includes the reduction of words such as "joyful" and "joyfulness" to the baseform "joy." These examples are provided for illustration purposes. Typical medical problems can have complex derivations and inflections, and may have a number of derivational and/or inflectional affixes.

Once the input string has been stemmed, non-content words may be filtered out of the input string. Alternatively, non-content words may be filtered out prior to the computation of the medical problem baseforms. Examples of medical non-content words include: "alongside," "an," "and," "anything," "around," "as," "at," "because," "chronically," "consists," "covered," "properly," "specific," "throughout," "to," "up," "while," and "without." This list is not intended to be exhaustive but is merely illustrative of possible non-content words that may be filtered out of an input string prior to scoring. Any number of non-content words are possible if the words are not significant in discriminating strings.

Once the baseforms of the text associated with the input string (e.g., the input medical problem) have been determined, a sorted list of the baseform transform may be produced, step 315. Within the sorted list, the stems may appear in a lexically sorted order, rather than in natural order. The use of lexically sorted order may be a computational convenience. Any other sort order could be used in connection with these methods. Approximation match processing may utilize this list in attempting to make further matches. In step 317, the system may set the value N to equal 1.

After the input string has been filtered and stemmed, the input string may be compared to a list of predetermined baseform sequences, step 320. These predetermined baseform sequences can be retrieved by referencing them through, for example, a baseform index, step 330. If the baseform is not in the baseform index, the system determines in step 332 whether all of the baseforms have been compared. If so, the system exits in step 339 to the nearest neighbor processing. If not, the system sets the value N to N+1 in step 325 and repeats step 320.

If any of the baseforms associated with the input string produce matches, a vector of predetermined baseform sequences referenced by the baseform index can be stored as in step 335, for example, in a memory device. The system then determines in step 337 whether all of the baseforms have been compared. If so the value M is set to 1 in step 340. If not, the value N is set to N+1 in step 323 and step 320 is repeated. As discussed above, the vector of entries may be associated with the number of times the baseform occurs within the predetermined classification scheme. The stored vector of baseform-matching entries can then be manipulated in a data structure and undergo a scoring process.

Exemplary data structures that may be used in connection with an embodiment of the invention may include a first data structure and a second data structure. The first data structure, referred to herein as a "candidate entry list item," can include two data fields. The first data field includes an entry number. This entry number may be uniquely associated with an entry for a particular element within the predetermined categorization scheme, such as, for example, an entry associated with a medical problem in the SNOMED CT nomenclature. The second field includes an integer associated with the entry number that may be used as a key for retrieving the entry associated with that entry number.

The second data structure, referred to herein as "scored entry list items," may include two data fields. The first data field may be the entry number, and the second data field may be a floating-point number associated with the entry number.

In addition to the data structures, two lists may be formed. The first list is referred to herein as the "candidate list." The second list is referred to herein as the "hit list," and is where the second entries can be listed. Initially, the hit list may be empty. These lists and data structures may be utilized in the scoring of the approximation processing step 130 results.

Entry information associated with the baseforms may now be retrieved from, for example, a memory device, and can be further processed. Each entry within the vector includes at least one associated entry number. If the entry number associated with the entry within the vector appears on the candidate list which includes all baseforms associated with the input string, step 345, then the integer associated with the entry may be extracted, step 348. If the entry number associated with the entry within the vector does not appear on the candidate list, a candidate entry list entry may be created, step 350 for the entry number associated with the entry within the vector, the associated integer may be compared in step 355, and a counter of the number of baseforms in both the input string and the given entry, may be set to, for example, 1, as shown in step 357. This allows the candidate list to contain the union of all entries that have at least one of the baseforms contained in the input problem, and in addition, the integer in each candidate list item counts the number of baseforms that entry has in common with the input problem.

In one embodiment, after the candidate list has been constructed such that the candidate list contains the union of all entry numbers that have at least one of the baseforms contained in the input problem, the candidate list may be sorted by the number of common baseforms, step 360. In one embodiment, the baseforms may be sorted in descending order. In an alternative embodiment, the baseforms may be sorted in ascending order.

Referring to FIG. 4B, step 360 may include for each item on the candidate list, the maximum possible field similarity score that may be achieved by each candidate may be computed in step 400. This may be performed based on the number of known baseforms in the input problem and the number of common baseforms shared by the candidate, step 405. In one embodiment, the field similarity algorithm may involve extensive comparisons to determine how many common baseforms are found in common between the input string and a candidate and their relative order. However, assuming that an input string and candidate deviate only in the number of common baseforms, but not order, permits computing the best possible field similarity score between a given input string and the associated candidate baseforms. This artificial score may set an upper bound on the similarity between a given input string and candidate baseforms; and candidates that do not achieve the minimal similarity score under the best of circumstances may be eliminated from further processing. This optimization does not necessarily affect the quality of the results, but may affect the performance of the algorithm.

The number determined by this calculation may be used as the score. In one embodiment, the score is compared to determine is it is lower than an algorithm field similarity threshold in step 410, which may be a predetermined threshold number, $T_{fs}$, the algorithm can stop further processing of the candidate list, step 415. This embodiment reveals one advantage of sorting the entries having the highest number of matching baseforms in descending order. If the top element on the list does not have a score exceeding the predetermined threshold score, then the remainder of the elements in the list will not exceed the predetermined threshold score, and the algorithm can perform an early exit without having to process the remainder of the candidates on the list. This is not intended to mean that an ascending order sort is not feasible, or would not be preferred where processing speed is not a critical feature. Additionally, the data within the candidate list need not be sorted at all in some embodiments. This may be feasible or appropriate in applications in which the size of the candidate lists are relatively small. However, in the case of matching SNOMED CT nomenclature terms, this optimization may provide a substantial reduction in both computation efficiency and memory usage.

If the score is above the predetermined threshold, the entry within the predetermined classification scheme associated with the candidate entry may be retrieved based on the entry number associated with the candidate entry, step 420. An actual field similarity score can then be calculated between the input string that has undergone a baseform transform and the candidate that has similarly undergone a baseform transform, with respect to natural order, step 425. An approximate string comparison technique that produces a score may also be applied rather than the field similarity algorithm Other possible algorithms include, but are not limited to Levenshtein edit distance or a variety of dissimilarity algorithms such as dice or cosine, the use of ngrams or other lexical features instead of words or baseforms. The sorted baseform can also be computed, step 430. A sorted baseform transform may involve sorting the output of the baseform transform. After the sorted baseform transform has been computed for the candidate, the actual field similarity between the input baseform and the candidate baseform can be determined with respect to sorted order, step 435. In step 440, if the maximum of either the natural order field similarity score, or the sorted order field similarity score is greater than a predetermined field similarity threshold score, then this entry may be inserted into the hit list, step 450. In one embodiment, the entry on the hit list may include the candidate's entry number, and the natural order field similarity as the associated floating point number, regardless of whether the field similarity score was above the threshold. The use of two forms of the input string (i.e., in natural and sorted order) may compensate for the limited representativeness of the candidate list, since it may not, in principle, contain all possible ways of expressing a given medical concept. If a variant representation were entered into, for example, a user dictionary or compiled into a, for example, master dictionary, then this representation may match in natural order better than a variant in sorted order. If, after computing the field similarity scores for each of the candidates that met or exceeded the predetermined threshold score, there were any candidates that scored above the field similarity threshold score, then there will be at least one item in the hit list. Otherwise, the hit list will be empty.

Referring now to FIG. 4C, in step 460, there is a determination of whether the hit list is empty after all of the vector entries have been scored, then the algorithm can exit at step 465. The algorithm may then proceed to nearest neighbor match processing step 140. If the hit list is not empty, the return list may be sorted based on the field similarity score, step 470. In one embodiment, the list may be sorted in descending order based on the score. In an alternative embodiment, the list may be sorted in ascending order. Any type of sorting may be used to sort the hit list. After the field similarity scores have been sorted, they may be scaled into an interval, step 475. In some embodiments, scaling may not be required. Scaling, however, may provide a consistent representation of the similarity to the user applications that can operate with the results of the matching process and may make a difference in the scores of candidates more comprehensible. These differences may be important in some applications, particularly where a user may prefer to display one candidate if the difference between the top score and the second score exceeds a given threshold. This exemplary computation may be simplified using scaling. One exemplary interval that the field similarity scores may be scaled to is [0.80, 0.95]. Other intervals may be used as appropriate.

After scaling, a list of returned codes may be created in step 480. The creation of the list of codes described herein applies to an embodiment in which the list of entry numbers have been sorted in descending order according to degree of match, with an associated floating point number. This floating point number may be scaled into some part of the interval (0, 0.95] that characterizes the relative degree of the match. In order to return appropriate codes, the list of entry numbers needs to be associated with a list of actual codes, with weights, which are to be returned by the algorithm.

For this purpose, the "scored code list item" data structure may be used. This data structure may include three fields. These fields may include the Dictaphone SNOMED CT Clinical Subset code; an associated floating-point weight; and a flag to indicate whether the code is a preferred code or not. A return list can be created to store any of the returned codes. For each item in the hit list, the corresponding entries in the predetermined categorization scheme can be looked up. If the entry has a preferred code, a return list item can be created for this code. The return list item for that code may include a weight that is the hit list weight. Additionally, the preferred flag indicator may be activated, or set to true. For each remaining code, additional return list items may be created. Like the initial return list item, the weight may be the hit list weight and the preferred flag may be deactivated, or set to false.

If the entry does not have a preferred code, a return list item may be created for the single code the entry does contain, where the weight is the hit list weight and the preferred flag is set to false.

This return list may then be sorted by code, by weight descending within code, and by the value of the preferred flag.

This list may then be transversed, and for entries including multiple occurrences of a given code, all but the entry with the highest weight and preferred flag value may be removed from the return list. This list may then be resorted by weight, and by the value of the preferred flag within the weight. The combination of score and preference may be computed by a number of alternative methods.

After the list of returned codes has been created, the list may be returned or outputted to, for example, a user instep 485, and the algorithm may exit in step 490. Alternatively, the list of codes may be returned to a memory device for later usage. The combination of score and preference could be computed by alternative methods.

In an alternative embodiment, the scoring may be performed by, for example, a dice overlap measure. In one embodiment, the dice overlap measure may have a default of 0.75. Any acceptable type of scoring may be used to score the input string. The results may be output to a user. In one embodiment, only the top 32 hits are output to a user. In an alternative embodiment, only the top 10 results are output to a user. In one embodiment, the results may be presented using a reverse priority queue, in which the best results appear at the top of the list, and the worst results appear at the bottom of the list.

Nearest neighbor match processing step 140, can include, for example, a pattern recognition algorithm designed to recognize patterns of text within the input string. In one embodiment, nearest neighbor match processing stage can include k-nearest-neighbor (k-NN) matching against lexical and semantic features within the input string. Once the input string is received into the nearest neighbor match processing step 140, single word and multi-word sequences of stemmed forms can be filtered for non-content tokens. Non-content tokens were discussed above with reference to approximation match processing 130. In one embodiment, multi-word sequences of stemmed forms can include word sequences that have been bounded by medical problem tags. In one embodiment, the medical problem tagger may perform a low-level textual analysis to identify possible medical problems and their semantic constituents. Alternatively, bounding and analysis may be performed using machine-learning classification algorithms. Nearest neighbor match processing stage processing can also observe the complete set of hypernyms supplied by this tagging process. This semantic tagging process can identify the most precise analysis possible for a given span of text, but may also provide all possible semantic hypernyms for a given analysis. For example, a body part identified as the ankle can also supply semantic information such as ANKLE-LEG-LOWEREXTREMITY-EXTREMITY. This hypernym information may allow for a given for to match concepts of increasing generality. This can be useful in the case of the SNOMED CT nomenclature in which a broad body location identifier (e.g., "lower extremity") is used instead of a specific body site (e.g., "ankle") that may be more likely to appear in naturalistic physician descriptions of medical problems. The nearest neighbor matching process may compute features using individual hypernyms (here ANKLE<LEG, LOWEREXTREMITY, and EXTREMITY) and their combinations with lexical terms.

By performing these steps, the list of candidate features associated with the input string may be limited to content-bearing tokens. These tokens are incorporated as bare features and also as features including possible hypernyms. The hypernyms alone may also be features. All tagging, including the problem core, may include one or more hypernyms. These core hypernyms may be derived mechanically from, for example, the Dictaphone SNOMED CT Clinical subset by identifying all possible clinical concepts (or alternatively, their clinical concept parents) that have a given string in, for example, a SNOMED CT description associated with that concept (i.e., the concept directly or indirectly through its children). In alternative embodiments, a developer or an end-user may determine these concepts.

Prior to the comparison of the feature transformation associated with the input string, data structures and lists may be created for scoring and further processing of the features. Data structures such as the candidate entry list item and the scored entry list items as discussed with reference to approximation match processing can be used. Furthermore, lists such as the candidate list and hit list described above may be utilized in the scoring process.

After the feature transformations within the input string have been computed, the feature transforms may be compared to the listing of predetermined features sequences within a feature index. Each feature within the input string's feature transform can then be referenced against the feature index. If the feature is found in the feature index, the vector associated with the feature transform can be stored in, for example, a memory.

Similar to the description of the second stage processing and scoring, each vector can then be further processed. Each entry number of the vector list can be compared to the candidate list. If the number appears on the candidate list, then the integer associated with that entry may be incremented. The feature counter may provide optimizations analogous to those described with above with reference to the fields similarity computation. This optimization, however, may be substantially more important for nearest neighbor matching because the number of features compared may be substantially larger than for field similarity. If the entry number does not appear on the candidate list, then a new candidate list entry for this entry number may be created. The integer associated with this candidate list entry may be set to 1.

As before, this method ensures that the candidate list contains the union of all entry numbers that have at least one feature in common with the input problem. Additionally, the integer in each candidate list item counts the number of features that entry have in common with the input problem.

In an embodiment of the invention that may be specific to highly complex nomenclatures, such as that existing in the medical field, further semantic processing may be required. The semantic processing may include selecting the feature from the input string that represents the core concept. This can be done by comparing the features in the input string to a list of semantic features stored in a semantic feature priority table to find the feature or features with the highest priority, as described above. If there is more than one top-priority feature, each of these features may be referenced against a feature weight table. The feature weight table may include a figure of merit associated with a particular feature or features. One such figure of merit includes the information gain ratio. In one embodiment of the invention, the feature with the highest information-gain ratio may be determined by referencing the highest-scoring feature against the feature weight table to determine which feature has the highest information-gain ratio. In alternative embodiments, matching learning classification techniques may be used to identify and rank core concepts.

Now, this "core concept feature" may be referenced against the candidate list. The list may be filtered by maintaining the candidates including the core concept feature, and eliminating those that do not contain the core concept feature. This method may reduce processing time for further processing of the features. Additionally, this method can limit the amount of search space that will need to be utilized. Furthermore, it can eliminate the possibility of returning results that do not accurately reflect the input string.

In one embodiment, the algorithm can be self-limiting and may include a look-up threshold. This may reflect the total number of features that nearest neighbor matching may be configured to reference in the feature index. The number of features within the candidate list can be determined, and if it exceeds a threshold, the number may be reduced. An exemplary method for reducing the candidate feature list includes sorting the feature candidate list be the number common features. This list can be sorted in for example, either ascending or descending order. Any other type of sorting can be used. In an embodiment where the features are sorted in descending order, if the top of the list contains elements that have more than one feature in common with the input string, then the candidate list can be truncated. The feature candidate list can be truncated, for example, such that the candidate list can include only those features with a maximum number of common features. For example, if the list contains entries with three, two, and one common feature, then only those entries having three common features need be maintained on the list.

The number of feature candidates on the feature candidate list may be compared with the lookup threshold again to determine if the reduced number of candidate features is below the threshold. If the number of feature candidates is still above the threshold, additional reductions may be performed.

In one embodiment, the number of feature candidates can be reduced by sorting the items on the frequency candidate list by a frequency associated with the entry string. This frequency data may be derived empirically by counting the number of times a given feature occurs in correlation to a given target string. This may provide not only a relative frequency of occurrence of the given feature, but may also impact its ability to discriminate among candidates for which it is a feature. This sort may be, for example, in either descending or ascending form. These frequencies may be retrieved from an entry frequency table. After sorting the list in this manner, the list may be truncated at the lookup threshold, based on the words that appear most often in, for example, documents reviewed by the normalization algorithm.

For each item remaining in the feature candidate list, the candidates can be looked up in the feature index. If the feature is found in the feature index, the distance between the candidate match and the input string may be determined. This distance may be defined as the square root of the sum of the squares of the weights of all the features that either appear in the input string but not in the candidate match or appear in the candidate match but not in the input string.

Thus, in nearest neighbor match processing step 140, the entries that are the most similar to the input string may be found heuristically, and then the best possible entries may be retrieved. The best possible entries include those that contain one or all of the core concepts and the greatest number of common features. This data may now be scored to determine the most relevant hits. This may be done by measuring and minimizing dissimilarity between the candidates and the input string. A dissimilarity in this context can be any feature that is found in the input string that is not found in the candidate string. Alternatively, a dissimilarity may include any feature that is found in the candidate, but not in the input sting.

After the distances between the candidate features and the input string have been determined, they may be placed in a hit list. A hit list entry can include an entry number, which may be, for example, the candidate entry number, and an associated floating-point number. The floating-point number may be based on the computed distance between the candidate match and the input string. After calculating the distances, the algorithm can determine if the hit list is empty. If the hit list is empty, an error message may be returned to a user. Alternatively, the algorithm may prompt the user for feedback to allow the system to learn the input string and store it in, for example, the literal index for future use. In an alternative embodiment, the input string can be stored in the user dictionary. In this manner, the algorithm may be adaptive and may effectively learn new input strings for later usage.

If the hit list contains one or more candidate features, the list may be sorted in, for example, ascending order. In one embodiment, the scores associated with the candidate features may then be inverted and scaled over the interval (0, 0.75]. As previously mentioned, scaling, is not necessary, but may be advantageous in some embodiments. Next, a list of return codes can be created in the manner described with reference to the approximation processing step 130. After the list has been created, it may be, for example, returned to a user and the algorithm may exit.

In one embodiment, the third stage always generates a list of ranked Clinical Subset codes. In an alternative embodiment, if the results produced in the third stage do not exceed a predetermined threshold, a warning may be generated to the user indicating that the input medical problem was not matched.

By implementing a normalization scheme as described herein, a great deal of generalization may be achieved. For example, the predetermined classification scheme may include a description of a disorder of an extremity—for example gangrene. If a diagnosis includes gangrene of the big toe, the classification scheme may identify that the big toe is part of the foot, which is part of the leg, which is part of a lower extremity, which is an extremity. This is performed using semantic labels and overall normalization of the input string. This may result in robust matching.

As mentioned previously, the normalization algorithm can be implemented as an incremental or adaptive learning algorithm, which permits the algorithm to become more efficient and attain earlier exits from the stages. In one embodiment, each time a particular string is matched after undergoing the nearest neighbor processing step 140, the string may be stored in a usage database. A determination may be made as to whether the usage has exceeded a predetermined threshold, which may be one or more usages of a particular string. If the threshold has been surpassed, the string may be promoted to the literal index to permit faster matching. If the threshold has not been crossed, the usage is noted in, for example, a lookup table, and this adaptive loop can terminate. In yet another embodiment, the string can be input into a user dictionary for comparison against future input strings using the user dictionary step processing as illustrated as described with respect to FIG. 2, 35. In an alternative embodiment, a user may be prompted to accept the promotion of a particular string into either the literal index or the user-defined dictionary.

Figure 5:
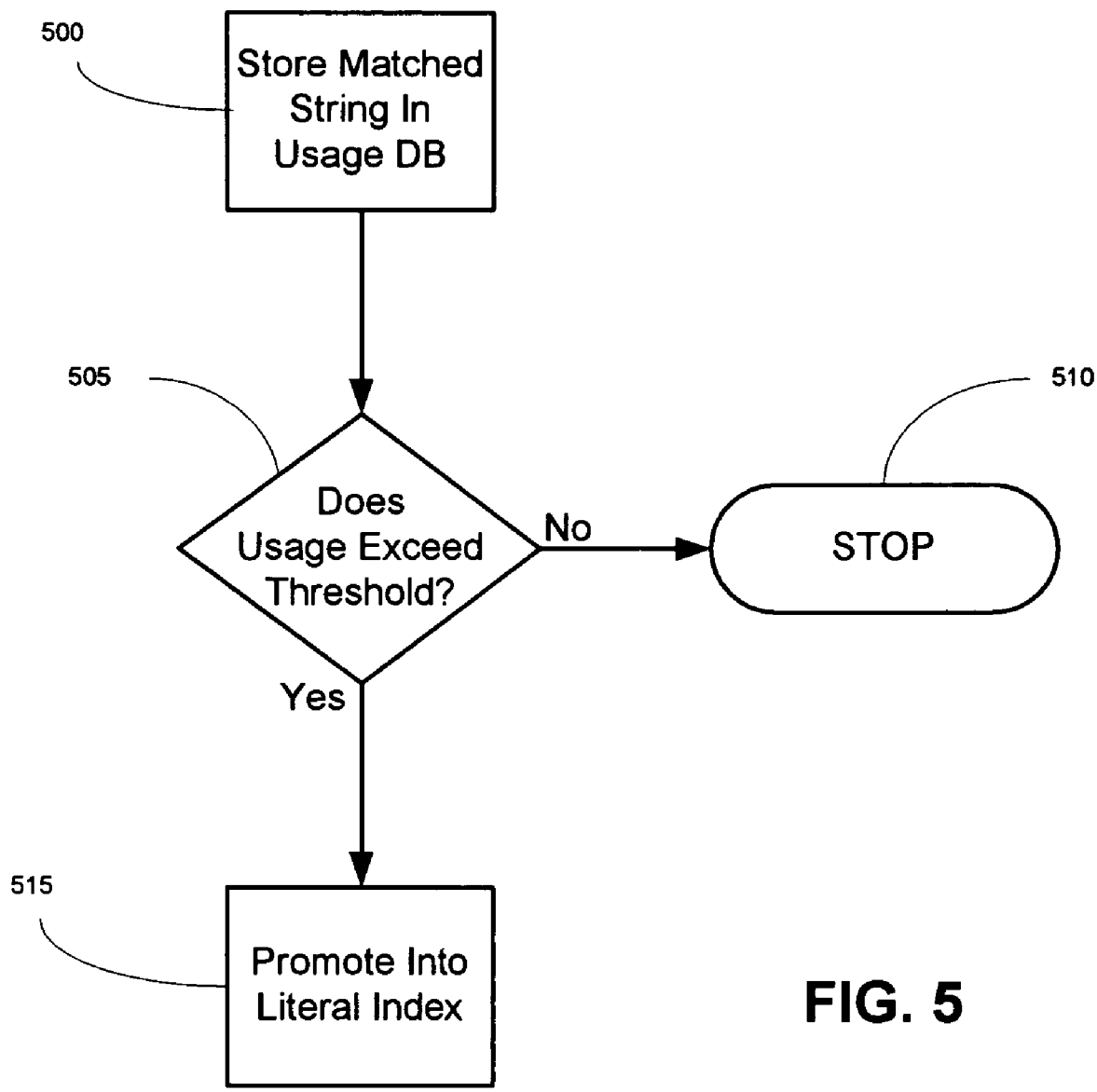
FIG. 5 shows an additional logic flow diagram detailing an additional process as shown in FIG. 1 according to one embodiment of the invention.

Referring to FIG. 5 the system may store the matched string in the usage database in step 500. If the usage exceeds the threshold, step 505, then string is promoted to the literal index in step 515. If not, the system stops at step 510.

The described algorithm and predetermined categorization scheme can be either service-based or client-based. Due to the large volume of data contained in the categorization scheme, for some applications it may be preferable to include the predetermined categorization scheme on a server, which may be accessible to individual clients. This arrangement can also enable more efficient data management. Additionally, in embodiments of the invention including an adaptive classification system, client-based systems can become increasingly difficult to maintain.

While various embodiments of the invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

For example, while tagging of input strings was described with reference to the utilization of XML as a mark-up language, any suitable markup language may be used. For example, HTML may be used.

Furthermore, while particular embodiments of the invention were described with respect to the use of the Dictaphone SNOMED CT Clinical Subset and the larger SNOMED CT nomenclature, it should be understood that the invention is applicable to any method of normalizing input strings for classification in a particular predetermined classification scheme. While medical diagnosis provides a real-world example having a predetermined and preclassified nomenclature, a number of different applications are possible. For example, in the field of chemistry and chemical engineering, complex molecules and compounds may have very complex names that may be stated in different ways. Therefore, the present methods and systems including normalization and classification of input strings may be equally applicable in this field. There are countless other possible applications of the normalization and classification system and method according to various aspects of the invention as described herein. Therefore, any description of the invention with respect to the Dictaphone SNOMED CT Clinical Subset has been by way of example only, and is in no way intended to limit the scope of the invention.

What is claimed is:

1. In a computer system, a method for use in a predetermined categorization scheme, comprising:
  normalizing a string of words utilizing a computer configured to perform the steps of:
    receiving an input string of text;
    tagging the string of text by annotating a string of words with labels marking the start and end of relevant portions of text;
    comparing said tagged strings of text to a literal index, the literal index including a plurality of predetermined text sequences;
    determining if the string of text matches at least one of the plurality of predetermined text sequences within the literal index;
    if the string of words does not match at least one of the plurality of predetermined text sequences:
      determining a baseform transform of the input string, said baseform transform derived by removing of noise words and stemming the remaining words using de-derivation and uninflection, said baseform transform including at least one baseform associated with the input string;
      preparing a sorted version of the baseform transform;
      comparing the at least one baseform to a baseform index, the baseform index including a plurality of predetermined baseform sequences;
      determining a score for each of the plurality of predetermined baseform sequences that substantially match the at least one baseform and outputting feedback for any baseforms that exceed a predetermined threshold score;

if no baseforms exceed the predetermined threshold score:

computing a feature transformation of the input string, the feature transform including at least one feature associated with the input string;

comparing the at least one feature to a feature index, the feature index including a plurality of predetermined feature sequences;

determining a score for each of the plurality of predetermined feature sequences that substantially match the at least one feature; and outputting a hit list of candidate sequence matches based on the input string, and if no feature sequences are found based on the input string, outputting an indication that no predetermined text sequences were found within the predetermined categorization scheme wherein the method is performed by a computer executing stored instructions.

2. An apparatus for normalizing a string of words for use in a predetermined categorization scheme, comprising:

a processor and a memory encoded with instructions, for execution by the processor, to receive an input string of text, to tag relevant portions of the input string by marking the beginning and the end of said relevant portions of the input string and by marking said relevant portions of the input string with semantic labels based on the predetermined categorization scheme, to compare the tagged portions of said input string to a literal index, where the literal index includes a plurality of predetermined text sequences, and to determine if the string of text matches at least one of the plurality of predetermined text sequences within the literal index; wherein if the string of words does not match at least one of the plurality of predetermined text sequences:

determining a baseform transform of the input string, said baseform transform derived by removing of noise words and stemming the remaining words using de-derivation and uninflection, said baseform transform including at least one baseform associated with the input string;

preparing a sorted version of the baseform transform;

comparing the at least one baseform to a baseform index, the baseform index including a plurality of predetermined baseform sequences;

determining a score for each of the plurality of predetermined baseform sequences that substantially match the at least one baseform and outputting feedback for any baseforms that exceed a predetermined threshold score;

if no baseforms exceed the predetermined threshold score:

computing a feature transformation of the input string, the feature transform including at least one feature associated with the input string;

comparing the at least one feature to a feature index, the feature index including a plurality of predetermined feature sequences;

determining a score for each of the plurality of predetermined feature sequences that substantially match the at least one feature; and outputting a hit list of candidate sequence matches based on the input string, and if no feature sequences are found based on the input string, outputting an indication that no predetermined text sequences were found within the predetermined categorization scheme.

\* \* \* \* \*